United States Patent [19]

Praefcke et al.

[11] 4,419,263

[45] Dec. 6, 1983

[54] LIQUID CRYSTALLINE CYCLOHEXYLCARBONITRILE DERIVATIVES

[75] Inventors: Klaus Praefcke; Dietmar Schmidt, both of Berlin; Rudolf Eidenschink, Dieburg, all of Fed. Rep. of Germany

[73] Assignee: Merck Patent Gesellschaft mit beschränkter Haftung, Darmstadt, Fed. Rep. of Germany

[21] Appl. No.: 337,805

[22] Filed: Jan. 7, 1982

[30] Foreign Application Priority Data

Jan. 7, 1981 [DE] Fed. Rep. of Germany ....... 3100142

[51] Int. Cl.³ .......................... C09K 3/34; G02F 1/13; C07C 121/46; C07C 121/66; C07C 120/00; C07C 120/04
[52] U.S. Cl. ........................ 252/299.63; 252/299.5; 260/464; 260/465 C; 260/465 D; 260/465 F; 260/465 R; 350/350 R
[58] Field of Search ........................ 252/299.63, 299.5; 260/464, 465 C, 465 D, 465 F, 465 R; 350/350 R

[56] References Cited

U.S. PATENT DOCUMENTS

| | | | |
|---|---|---|---|
| 4,035,056 | 7/1977 | Coates et al. | 252/299.66 |
| 4,154,697 | 5/1979 | Eidenschink et al. | 252/299.63 |
| 4,181,625 | 1/1980 | Eidenschink et al. | 252/299.63 |
| 4,228,029 | 10/1980 | Osman | 252/299.5 |
| 4,229,315 | 10/1980 | Krause et al. | 252/299.63 |
| 4,261,651 | 4/1981 | Gray et al. | 252/299.63 |
| 4,293,434 | 10/1981 | Deutscher et al. | 252/299.63 |
| 4,349,452 | 9/1982 | Osman et al. | 252/299.63 |
| 4,357,078 | 11/1982 | Carr et al. | 252/299.63 |
| 4,361,494 | 11/1982 | Osman et al. | 252/299.63 |
| 4,368,135 | 1/1983 | Osman | 252/299.63 |

FOREIGN PATENT DOCUMENTS

| | | | |
|---|---|---|---|
| 23730 | 2/1981 | European Pat. Off. | 252/299.63 |
| 30761 | 6/1981 | European Pat. Off. | 252/299.63 |
| 58512 | 8/1982 | European Pat. Off. | 252/299.63 |
| 57-48945 | 3/1982 | Japan | 252/299.63 |
| 2082179 | 3/1982 | United Kingdom | 252/299.62 |
| 2084576 | 4/1982 | United Kingdom | 252/299.62 |
| 2086385 | 5/1982 | United Kingdom | 252/299.63 |
| 2092146 | 8/1982 | United Kingdom | 252/299.63 |

OTHER PUBLICATIONS

Osman, M. A. et al., Mol. Cryst. Liq. Cryst., vol. 72, (Lett.), pp. 89–94, (1981).
Osman, M. A. et al., Mol. Cryst. Liq. Cryst., vol. 56, (Lett.), pp. 105–109, (1979).
Osman, M. A., Mol. Cryst. Liq. Cryst., vol. 82, (Lett.), pp. 47–52, (1982).
Gray, G. W. et al., Mol. Cryst. Liq. Cryst., vol. 53, pp. 147–166, (1979).
Praefcke, K. et al., Chemiker-Zeitung, vol. 105, No. 1, pp. 8–9, (Jan. 1981).
Praefcke, K. et al., Chemiker-Zeitung, vol. 104, No. 9, pp. 269–271, (1980).
Praefcke, K. et al., Z. Naturforsch, vol. 356, pp. 1451–1454, (1980).
Osman, M. A., Mol. Cryst. Liq. Cryst., vol. 72, (Letters), pp. 291–295, (1982).
"Deutscher, H. J. et al., Advances in Liquid Crystal Research and Applications," Bata, L., Ed., Pergamon Press, Oxford, pp. 1075–1079, (1980).
"Demus, D. et al., Mol. Cryst. Liq. Cryst.," vol. 63, pp. 129–144, (1981).

Primary Examiner—Teddy S. Gron
Attorney, Agent, or Firm—Millen & White

[57] ABSTRACT

Cyclohexylcarbonitrile derivatives of the formula I

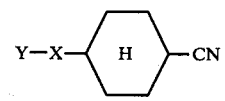

wherein Y is

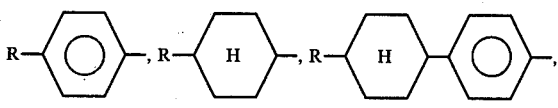

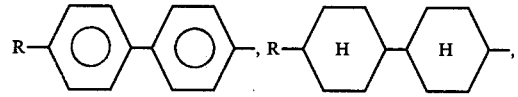

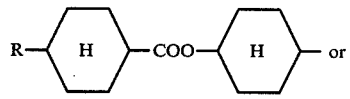

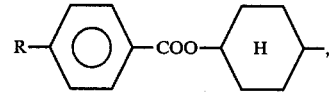

X is —COO—, —O—CO, —CH₂O—, —OCH₂— or —CH₂CH₂—, and R is alkyl or alkoxy each of 1–12 carbon atoms, with the proviso that Y is not

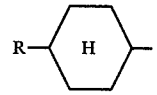

when X is —COO—; and all cyclohexyl rings are trans, are valuable liquid crystalline components.

20 Claims, No Drawings

LIQUID CRYSTALLINE CYCLOHEXYLCARBONITRILE DERIVATIVES

BACKGROUND OF THE INVENTION

The properties whereby nematic or nematic-cholesteric liquid-crystalline materials significantly change their optical properties, such as light absorption, light scattering, birefringence, reflectance or color, under the influence of electric fields are utilized to a great extent for electro-optical display elements. The functioning of display elements of this type is based, for example, on the phenomena of dynamic scattering, the deformation of aligned phases, the Schadt-Helfrich effect in the twisted cell or the cholesteric-nematic phase transition.

For the technical application of these effects in electronic components, liquid-crystalline dielectrics are required which must fulfill a large number of requirements. Chemical stability to moisture, air and physical effects, such as heat, radiation in the infrared, visible and ultraviolet ranges, and direct current and alternating electric fields, are of particular importance. Industrially usable liquid-crystalline dielectrics are also required to have a liquid-crystalline mesophase in the temperature range from at least $+10°$ C. to $+50°$ C., preferably 0° C. to 60° C., and as low a viscosity as possible at room temperature, which preferably should not be more than $70.10^{-3}$ Pa.s. Finally, they must not have any characteristic absorption in the visible range, i.e., they must be colorless.

A number of liquid-crystalline compounds has already been disclosed, which fulfill the stability requirements of dielectrics intended for electronic components, and which are also colorless. These include, in particular, the p,p'-disubstituted phenylbenzoates described in German Offenlegungsschrift No. 2,139,628 and the p,p'-disubstituted phenylcyclohexane derivatives described in German Offenlegungsschrift No. 2,636,684. In these two classes of compounds, and also in other known series of compounds with a liquid-crystalline mesophase, there are no individual compounds which form a liquid-crystalline nematic mesophase in the required temperature range from 10° C. to 60° C. As a rule, mixtures of two or more compounds are therefore prepared in order to obtain substances which can be used as liquid-crystalline dielectrics. For this purpose, at least one compound having a low melting point and clear point is usually mixed with another compound having a markedly higher melting point and clear point. This normally gives a mixture whose melting point is below that of the lower-melting component, while its clear point is between the clear points of the components. However, the preparation of optimum dielectrics constantly causes difficulties, since the components having the high melting points and clear points frequently also impart a high viscosity to the mixtures. As a result, the switching times of the electro-optical display elements produced with these mixtures, are extended in an undesirable manner. In addition, problems often occur owing to the fact that the solubility of the various components in one another, particularly at room temperature or lower temperatures, is only very limited.

SUMMARY OF THE INVENTION

Accordingly, it is an object of this invention to provide liquid-crystalline dielectrics which have a nematic phase in the required temperature range and which enable sufficiently short switching times in liquid crystal cells at room temperature.

Upon further study of the specification and appended claims, further objects and advantages of this invention will become apparent to those skilled in the art.

These objects have been obtained by providing cyclohexylcarbonitrile derivatives of formula (I)

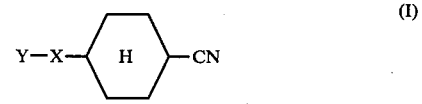

wherein Y is

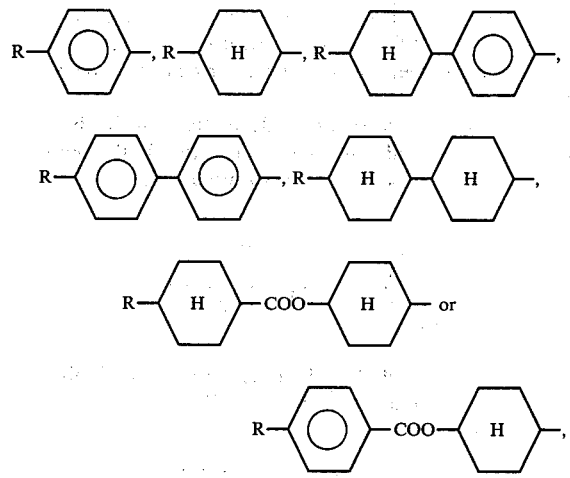

X is —COO—, —O—CO—, —CH₂O—, —OCH₂— or —CH₂CH₂—, and R is alkyl or alkoxy each of 1-12 carbon atoms, Y, however, not being

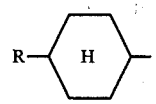

when X is —COO—; and all cyclohexyl rings being trans.

The present invention thus relates to the cyclohexylcarbonitrile derivatives of formula (I) and to their use as components of liquid-crystalline dielectrics. Furthermore, the present invention relates to liquid-crystalline dielectrics containing at least one cyclohexylcarbonitrile derivative of formula (I) and to electro-optical display elements which are based on a liquid crystal cell and which contain a liquid-crystalline dielectric of this type.

DETAILED DISCUSSION

These cyclohexylcarbonitrile derivatives of formula (I) are outstandingly suitable as components of liquid-crystalline dielectrics. They have an extraordinarily wide range of application. Depending on the choice of the substituents, the compounds of formula (I) can be used as base materials for liquid-crystalline dielectrics. The latter can be exclusively or predominantly composed of these compounds; but it is also possible to add compounds of formula (I), in smaller proportions of, for example, 2 to 45 percent by weight, to liquid-crystalline base materials of other classes of compounds to prepare dielectrics with an extended liquid-crystalline mesophase, or to influence the extent of the dielectric anisotropy of such a dielectric.

By suitable choice of the groups X and Y, in the compounds of formula (I), it is possible to prepare dielectrics with a pronounced positive dielectric anisotropy for use in display elements based on the principle of the twisted nematic cell or the cholesteric-nematic phase transition. It is also possible to prepare dielectrics which have a dielectric anisotropy differing only slightly from zero, and which are used in display elements based on the principle of dynamic scattering or the deformation of aligned phases (DAP effect).

In the pure state, the compounds of formula (I) are colorless and form nematic mesophases within a temperature range which is astonishingly wide and in a favorable region for electro-optical use.

In the formulae, all cyclohexane rings are trans-substituted.

The cyclohexylcarbonitrile derivatives of this invention comprise trans-4-cyanocyclohexyl 4-alkylbenzoates and 4-alkoxybenzoates of formula (Ia),

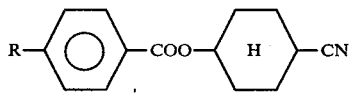

trans-4-cyanocyclohexyl 4-(trans-4-alkyl)- and alkoxycyclohexyl)-benzoates of formula (Ib),

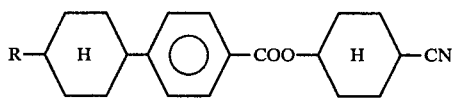

trans-4-cyanocyclohexyl 4-alkyl- and alkoxybiphenyl-4'-carboxylates of formula (Ic),

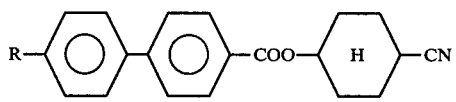

all-trans-4-cyanocyclohexyl-4-(4-alkyl- and alkoxycyclohexyl)-cyclohexanecarboxylates of formula (Id),

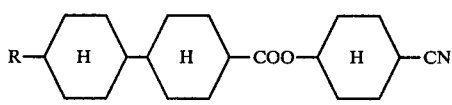

all-trans-4-cyanocyclohexyl-4-(4-alkyl- and -alkoxycyclohexanoyloxy)-cyclohexanecarboxylates of formula (Ie),

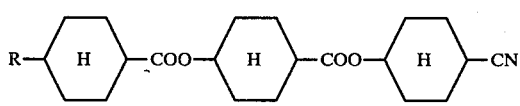

4-alkyl- and alkoxyphenyl trans-4-cyanocyclohexanecarboxylates of formula (If),

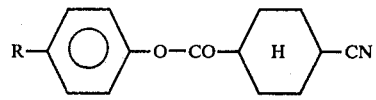

trans-4-alkyl- and alkoxycyclohexyl trans-4-cyanocyclohexanecarboxylates of formula (Ig),

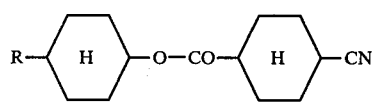

4-(trans-4-alkyl- and alkoxycyclohexyl)-phenyl trans-4-cyanocyclohexanecarboxylates of formula (Ih),

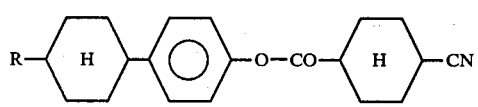

all-trans-4-(4-alkyl- and alkoxycyclohexyl)-cyclohexyl-4-cyanocyclohexanecarboxylates of formula (Ii),

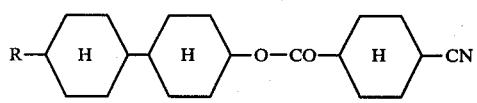

all-trans-4-(4-alkyl- and alkoxycyclohexanoyloxy)-cyclohexyl-4-cyanocyclohexanecarboxylates of formula (Ik),

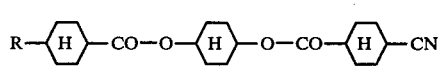

4-alkyl- and alkoxybiphenyl-4'-yl trans-4-cyanocyclohexanecarboxylates of formula (Il),

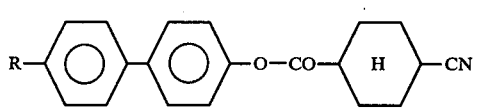

4-alkyl- and alkoxybenzyl trans-4-cyanocyclohexyl ethers of formula (Im),

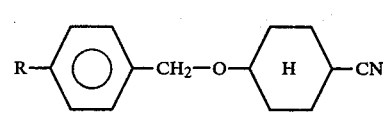

trans-4-alkyl- and alkoxycyclohexylmethyl trans-4-cyanocyclohexyl ethers of formula (In),

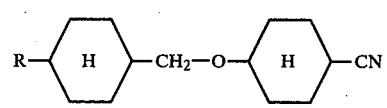

4-(trans-4-alkyl- and alkoxycyclohexyl)-benzyl trans-4-cyanocyclohexyl ethers of formula (Io),

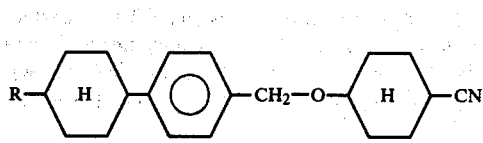

4-(4-alkyl- and alkoxyphenyl)-benzyl trans-4-cyanocyclohexyl ethers of formula (Ip),

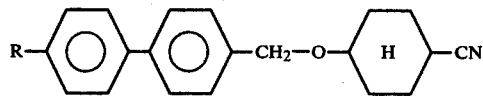

all-trans-4-(4-alkyl- and alkoxycyclohexyl)-cyclohexylmethyl 4-cyanocyclohexyl ethers of formula (Iq),

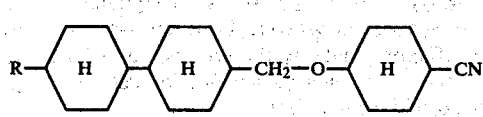

all-trans-4-(4-alkyl- and alkoxycyclohexanoyloxy)-cyclohexylmethyl 4-cyanocyclohexyl ethers of formula (Ir),

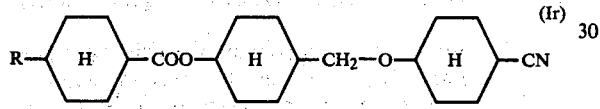

trans-4-cyanocyclohexylmethyl 4-alkyl- and alkoxyphenyl ethers of formula (Is),

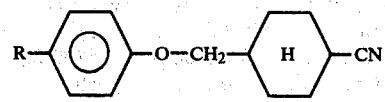

trans-4-cyanocyclohexylmethyl trans-4-alkyl- and alkoxycyclohexyl ethers of formula (It),

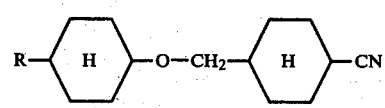

trans-4-cyanocyclohexylmethyl 4-(trans-4-alkyl- and alkoxy-cyclohexyl)-phenyl ethers of formula (Iu),

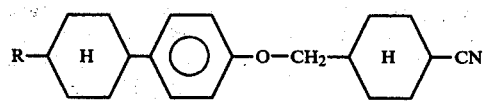

all-trans-4-cyanocyclohexylmethyl 4-(4-alkyl- and alkoxycyclohexyl)-cyclohexyl ethers of formula (Iv),

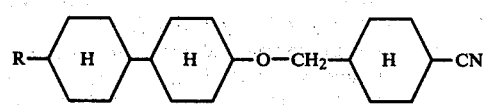

trans-4-cyanocyclohexylmethyl 4-alkyl- and alkoxybiphenyl-4'-yl ethers of formula (Iw),

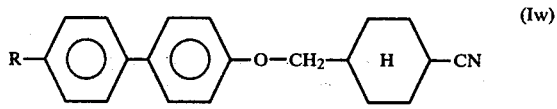

all-trans-4-cyanocyclohexylmethyl 4-(4-alkyl- and alkoxycyclohexanoyloxy)-cyclohexyl ethers of formula (Ix),

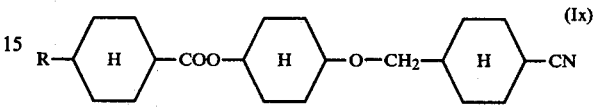

1-(4-alkyl- and alkoxyphenyl)-2-(trans-4-cyanocyclohexyl)-ethanes of formula (Iy),

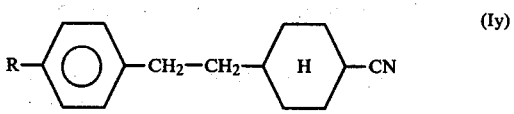

1-(trans-4-alkyl- and alkoxycyclohexyl)-2-(trans-4-cyanocyclohexyl)-ethanes of formula (Iz),

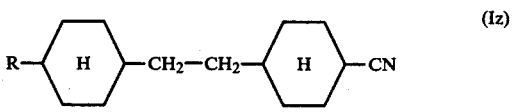

1-[4-(trans-4-alkyl- and alkoxycyclohexyl)-phenyl]-2-(trans-4-cyanocyclohexyl)-ethanes of formula (Iaa),

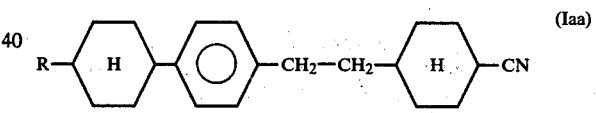

all-trans-1-[4-(4-alkyl- and alkoxycyclohexyl)-cyclohexyl]-2-(4-cyanocyclohexyl)-ethanes of formula (Ibb),

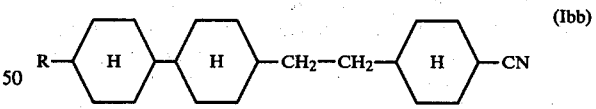

1-(4-alkyl- and alkoxybiphenyl-4'-yl)-2-(trans-4-cyanocyclohexyl)-ethanes of formula (Icc),

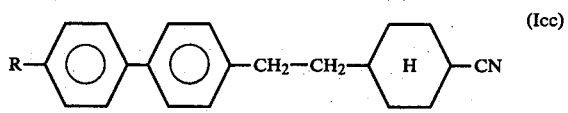

all-trans-1-[4-(4-alkyl- and alkoxycyclohexanoyloxy)-cyclohexyl]-2-(4-cyanocyclohexyl)-ethanes of formula (Idd),

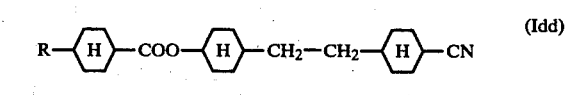

trans-4-(4-alkyl- and alkoxybenzoyloxy)-1-(4-trans-cyanocyclohexanoyloxy)-cyclohexanes of formula (Iee),

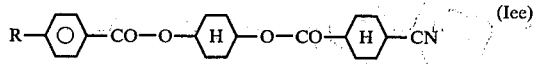

trans-4-cyanocyclohexyl trans-4-(4-alkyl- and alkoxybenzoyloxy)-cyclohexanecarboxylates of formula (Iff),

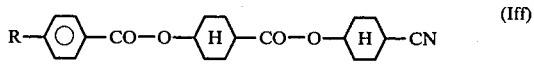

trans-4-(4-alkyl- and alkoxybenzoyloxy)-cyclohexylmethyl trans-4-cyanocyclohexyl ethers of formula (Igg),

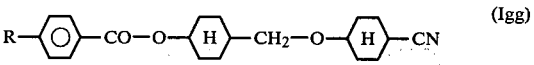

trans-4-cyanocyclohexylmethyl trans-4-(4-alkyl- and alkoxybenzoyloxy)-cyclohexyl ethers of formula (Ihh),

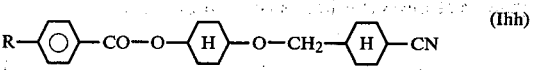

and 1-[trans-4-(4-alkyl- and alkoxybenzoyloxy)-cyclohexyl]-2-(trans-4-cyanocyclohexyl)-ethanes of formula (Iii)

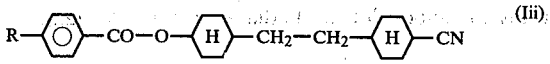

In the compounds of formula (I), the alkyl or alkoxy or radical R can be straight chained or branched. If it is straight chained, i.e., is methyl, ethyl, n-propyl, n-butyl, n-pentyl, n-hexyl, n-heptyl, n-octyl, n-nonyl, n-decyl, n-undecyl or n-dodecyl, the resultant compounds, as a rule, have higher clear points than those having a branched wing group R, and are therefore preferred. Compounds of formula (I) which have a branched wing group R are sometimes important because of a higher solubility in the conventional liquid-crystalline base materials, but particularly as chiral doping substances, if they possess optical activity due to the chain branching. Such branched wing groups R generally do not contain more than one chain branching. Preferred branched radicals R are those in which a methyl or ethyl group is located in the 1-, 2- or 3-position on a relatively long carbon chain, for example 2-methylpropyl, 2-methylbutyl, 3-methylbutyl, 2-methylpentyl, 3-methylpentyl, 2-ethylhexyl or 1-methylhexyl, as well as the corresponding alkoxy groups.

The preferred chain lengths of the wing groups R differ depending on the structure of the group Y. If Y is 4-R-phenyl, R is preferably alkyl of 2 to 11, particularly 3 to 8 carbon atoms or alkoxy of 1 to 10 carbon atoms. If Y is 4-R-cyclohexyl, alkyl groups of 3 to 10 carbon atoms are preferred as the alkyl groups and alkoxy groups of 2 to 8 carbon atoms are preferred as the alkoxy groups. If the group Y is 4-R-biphenyl-4'-yl, 4-(4-R-cyclohexyl)-phenyl or 4-(4-R-cyclohexyl)-cyclohexyl, the wing group R is preferably alkyl of 2 to 8 carbon atoms or alkoxy having 1 to 6 carbon atoms. These radicals R are also the preferred radicals if Y is 4-(4-alkyl- or alkoxycyclohexanoyl- or benzoyl-oxy)-cyclohexyl.

The compounds of this invention can be prepared in a manner which is conventional for substances of this type. Thus, the esters of formulae (Ia) to (II) are preferably prepared by reacting a trans-4-cyanocyclohexane derivative of the formula (II)

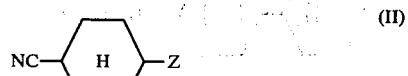

wherein Z is OH, OMe, COOH or a reactive derivative of the carboxyl group, and Me is an equivalent of a metal cation, at a temperature between −50° C. and +250° C., if appropriate, in the presence of an organic solvent and/or a customary esterification catalyst, with a compound of formula (III)

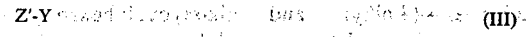

wherein Z' is COOH or a reactive derivative of the carboxyl group if Z is OH or OMe, and Z' is OH or OMe if Z is COOH or a reactive carboxyl group derivative.

In this process, the compounds of partial formulae (Ia) to (Ie) and (Iff) are obtained if Z is an hydroxyl group or an alcoholate group, preferably an alkali metal alcoholate group or alkaline earth metal alcoholate groups. The group Z' in the compounds of formula (III) is, in this case, —COOH or a reactive carboxyl group derivative, preferably —CO-halogen, particularly —COCl or —COBr, —COO-lower alkyl, particularly —COOCH₃, or an anhydride grouping, particularly a mixed anhydride, such as, for example, —COOCOCH₃.

Correspondingly, the compounds of partial formulae (If) to (Il) and (Iee) are formed if Z is COOH or a reactive carboxyl group derivatives and Z' is a hydroxyl group or alcoholate group. The reaction conditions are largely determined by the nature of the groups Z and Z': thus, a carboxylic acid is reacted with an alcohol (Z, Z'=COOH, OH), as a rule, in the presence of a strong acid, for example a mineral acid, such as hydrochloric acid or sulfuric acid. The reaction of an acid anhydride or, in particular, of an acid-chloride with an alcohol (Z, Z'=COCl, OH) is a preferred mode of reaction. These esterification reactions are preferably carried out in a basic medium, particularly alkali metal hydroxides, such as sodium or potassium hydroxide, alkali metal carbonates or bicarbonates, such as sodium carbonate, sodium bicarbonate, potassium carbonate or potassium bicarbonate, alkali metal acetates, such as sodium or potassium acetate, alkaline earth metal hydroxides, such as calcium hydroxide, or organic bases, such as triethylamine, pyridine, 4-dimethylaminopyridine or quinoline, being of importance as bases.

The esterifications are advantageously carried out in the presence of an inert solvent. Particularly well suited are ethers, such as diethyl ether, di-n-butyl ether, tetrahydrofuran, dioxane or anisole, ketones, such as acetone, butanone, pentan-3-one or cyclohexanone, amides, such as dimethylformamide or hexamethylphosphoric acid triamide, hydrocarbons such as benzene, toluene or xylene, halogeno-hydrocarbons, such as carbon tetrachloride or dichloromethane, and sulfoxides, such as dimethyl sulfoxide or sulfolane. Water-immiscible solvents can, at the same time, advantageously be used for azeotropically distilling off the water formed during the esterification. Occasionally, an excess of an organic base employed, for example pyridine, quinoline or triethylamine, can also be used as the solvent for the esterification. In principle, the esterification reactions can also be carried out in the absence of a solvent, for example by simply heating the components in the presence of sodium acetate.

The reaction temperature is usually between −50° C. and +250° C., preferably between −20° C. and +80° C. At these temperatures, the esterification reactions have ended, as a rule, after 15 minutes to 48 hours.

A further preferred embodiment, comprises first converting the alcohol to be esterified, of the formula II or III (Z or Z′=OH), into its sodium or potassium salt, for example by treatment with ethanolic sodium hydroxide solution or potassium hydroxide solution; isolating this salt and suspending it, together with sodium bicarbonate or potassium carbonate, in acetone or diethyl ether, while stirring; and adding dropwise to this suspension, while stirring, a solution of an acid-chloride or anhydride in diethyl ether, acetone or dimethylformamide. In this process, the reaction mixture is maintained at a temperature between −25° C. and +20° C., preferably at −10° C. to −20° C. In this procedure, the esterification reaction has usually ended after 15 to 50 minutes.

The ethers of the formulae (Im) to (Iw), with the exception of the compounds (Ir), can be prepared, for example, by a process in which, in an ester of the formula (IV)

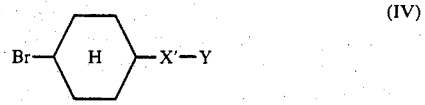

(IV)

wherein X′ is —COO— or —OCO— and Y is as defined in formula (I), with the exception of the trans-4-(trans-4-R-cyclohexanoyloxy)-cyclohexyl grouping and the trans-4-(4-R-benzoyloxy)-cyclohexyl grouping, the ester carbonyl group is reduced to the methyl group, for example using sodium borohydride and boron trifluoride, and the bromine atom is then replaced by the cyano group, in a manner which is conventional per se, for example by reaction with a metal cyanide in an aqueous-alcoholic solution.

In the synthesis of the ethers of formulae (Ir), (Ix), (Igg) and (Ihh), an ester of formula (V)

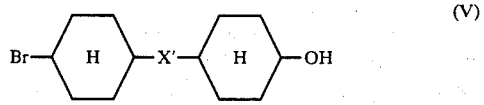

(V)

wherein X′ is as defined in formula (IV), is first reduced in an analogous manner, and Br is replaced by CN; the hydroxyl group is then esterified, in a manner which is customary per se, with 4-R-cyclohexanecarboxylic acid or a reactive derivative of this acid.

The 1,2-disubstituted ethanes of formulae (Iy) to (Icc) can be prepared, for example, by a process in which 4-cyanocyclohexanone is reacted with a Grignard compound of formula VI

(VI)

wherein Hal is Cl, Br or I and Y is as defined in formula (I), with the exception of the 4-(trans-4-R-cyclohexanoyloxy)-cyclohexyl grouping, the alcohol obtained after hydrolysis, of formula (VII),

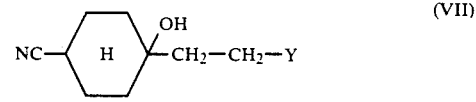

(VII)

is dehydrated, and, in the mixture of cyclohexene or ethylidenecyclohexane compounds formed thereby, the C=C double bond is selectively hydrogenated, for example with diimine. The preparation of the compounds of formulae (Idd) and (Iii) is effected analogously; a compound (VIa)

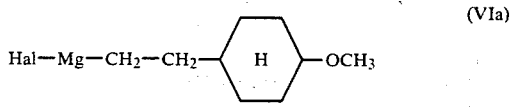

(VIa)

is employed, however, instead of the Grignard compound (IV); in this process, the methyl ethyl group is split off after the diimine reduction, and the resulting hydroxyl group is esterified using 4-R-cyclohexanecarboxylic acid or a reactive derivative thereof.

Some of the starting compounds, of formulae (II) to (VIa), employed in the synthesis described are known, and some of them can be prepared, in all cases in a manner which is customary per se, analogously to the known starting compounds, according to standard processes of preparative organic chemistry.

The liquid-crystalline dielectrics of this invention comprise two or more components, including at least one formula (I); it is also possible, however, for dielectrics of this invention to contain exclusively compounds of formula (I)—apart from optionally additionally present doping substances or additives, which themselves are not necessarily also liquid-crystalline. Optionally used additional components are preferably nematic or nematogenic substances from the classes comprising azobenzenes, azoxybenzenes, biphenyls, optionally partially hydrogenated terphenyls or quaterphenyls, Schiff's bases, particularly benzylidene derivatives, phenyl benzoates, phenyl pyrimidines, phenylcyclohexanes, optionally halogenated stilbenes, diphenylacetylene derivatives, diphenylnitrones, phenylnaphthalenes or cyclohexylnaphthalenes, which can be partially hydrogenated also in the naphthalene portion or can contain nitrogen atoms, and substituted cinnamic acids. The most important compounds which are suitable as additional components of this type can be characterized by formula (VIII):

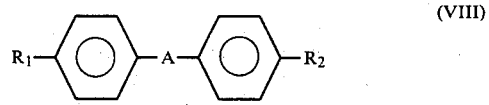

(VIII)

wherein A is

-CH=CH—

-continued

—CM=CH—
—CH=CM—
—C≡C—

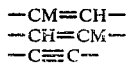  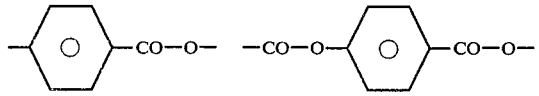

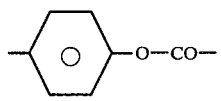

N=N—

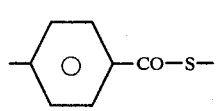

—N(O)=N—
—N=N(O)—
—CH₂—CH₂—
—OCO—

—CH=N—
—N=CH—
—CH₂—O—

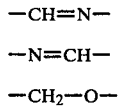

—CO—O—
—S—CO—
—CO—S—

—O—CH₂—
—CH=N(O)—
—N(O)=CH—

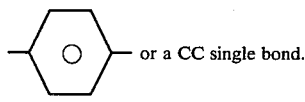 or a CC single bond.

Further possible components of the dielectrics of this invention are those compounds of formula (VIII) in which one or more phenyl rings are replaced by an appropriate number of trans-cyclohexyl rings; in addition, it is also possible for one of these rings to be a 2,5-disubstituted pyrimidine ring, or an optionally partially hydrogenated 2,6-disubstituted naphthalene or quinazoline system.

M is halogen, preferably Cl, or —CN. $R_1$ and $R_2$ are identical or different and can be alkyl, alkoxy, alkanoyl, alkanoyloxy or alkoxycarbonyloxy radicals having up to 18, preferably up to 8, C atoms; furthermore, it is also possible for one of these radicals to be trans-4-alkylcyclohexyl, —CN, —NC, —NO₂, —CF₃ or halogen.

In most of these compounds, $R_1$ and $R_2$ are preferably different, one of the radicals being, in the main, an alkyl or alkoxy group. However, a large number of other variants of the substituents envisaged are also customary. Many such substances are commercially available.

The dielectrics of this invention contain, as a rule, at least 30, preferably 50-99, particularly 60-98 percent by weight of the compounds of formula (I) and, optionally, (VIII). Of this proportion, at least 5 percent by weight, usually even 10 or more percent by weight, is preferably one or more compounds of formula (I). The invention also comprises those liquid-crystalline dielectrics to which only less than 5 percent by weight, for example 0.1 to 3 percent by weight, of one or more compounds of formula (I) have been added, for example for doping purposes.

The preparation of the dielectrics according to the invention is carried out in a manner which is conventional per se. As a rule, the desired quantity of the components used in a smaller quantity is dissolved in the component representing the main constituent, advantageously at elevated temperature. If a temperature above the clear point of the main constituent is chosen, the completeness of the solution process can be observed with particular ease.

It is also possible, however, to mix solutions of the component of formula (I) and, optionally, (VIII) in a suitable organic solvent, for example acetone, chloroform or methanol, and, after thorough mixing, to remove the solvent again, for example by distillation under reduced pressure. Of course, it it necessary in this procedure to take care that no impurities or undesired doping substances are introduced by the solvent.

The liquid-crystalline dielectrics of this invention can be modified by suitable additives in such a way that they can be used in all hitherto disclosed types of liquid crystal display elements. Additives of this type are known to those skilled in the art and are extensively described in the relevant literature. For example, substances can be added for varying the dielectric anisotropy, the optical anisotropy, the viscosity, the conductivity and/or the orientation of the nematic phases. Substances of this type are described, for example, in German Offenlegungsschriften Nos. 2,209,127, 2,240,864, 2,321,632, 2,338,281, 2,535,046, 2,637,430, 2,702,598, 2,900,312 and 3,000,375, whose disclosures are incorporated by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

In the examples, m.p. denotes the melting point, and c.p. denotes the clear point, of a liquid-crystalline substance in degrees centigrade; boiling points are designated by b.p.

EXAMPLE 1

A solution of 2.1 g of 4-n-pentylbenzoyl chloride in 20 ml of dichloromethane is added dropwise to a solution of 1.25 g of trans-4-cyanocyclohexanol and 1.5 g of 4-dimethylaminopyridine in 50 ml of dichloromethane at room temperature, while stirring. The reaction mixture is stirred for 2 hours at room temperature, the solvent is distilled off under reduced pressure, the residue is taken up in 100 ml of diethyl ether, the resulting solution is extracted by shaking successively with 20 ml each of 2 N hydrochloric acid and 5% aqueous sodium bicarbonate solution, and the organic phase is dried over magnesium sulfate. The trans-4-cyanocyclohexyl 4-n-pentylbenzoate which remains after evaporation is recrystallized from ethanol; m.p. 28°, c.p. −6° (monotropic).

The following compounds are prepared analogously: trans-4-cyanocyclohexyl 4-n-heptylbenzoate, m.p. 53°, c.p. −8°; trans-4-cyanocyclohexyl 4-n-nonylbenzoate, m.p. 39°, c.p. −5°; trans-4-cyanocyclohexyl 4-ethoxybenzoate, trans-4-cyanocyclohexyl 4-n-octyloxybenzoate, trans-4-cyanocyclohexyl 4-n-propylbiphenyl-4'-carboxylate, trans-4-cyanocyclohexyl 4-n-hexylbiphenyl-4'-carboxylate, trans-4-cyanocyclohexyl 4-(2-methylbutyl)-biphenyl-4'-carboxylate, trans-4-cyanocyclohexyl 4-n-butyloxybiphenyl-4'-carboxylate, trans-4-cyanocyclohexyl 4-n-pentyloxybiphenyl-4'-carboxylate, 4-cyanocyclohexyl all-trans-4-(4-n-propylcyclohexyl)-cyclohexanecarboxylate, 4-cyanocyclohexyl all-trans-4-(4-n-heptylcyclohexyl)-cyclohexanecarboxylate, trans-4-cyanocyclohexyl 4-(trans-4-n-pentylcyclohexyl)-benzoate, m.p. 104°, c.p. 138°; trans-4-cyanocyclohexyl 4-(trans-4-n-propylcyclohexyl)-benzoate, m.p. 104°, c.p. 145°; trans-4-cyanocyclohexyl 4-(trans-4-n-heptylcyclohexyl)-benzoate, m.p. 99°, c.p. 133°; trans-4-cyanocyclohexyl 4-(trans-4-methoxycyclohexyl)-benzoate, 4-cyanocyclohexyl all-trans-4-(4-ethylcyclohexanoyloxy)-cyclohexanecarboxylate, 4-cyanocyclohexyl all-trans-4-(4-n-butylcyclohexanoyloxy)-cyclohexanecarboxylate, 4-ethylphenyl trans-4-cyanocyclohexanecarboxylate, 4-n-pentylphenyl trans-4-cyanocyclohexanecarboxylate, 4-n-decylphenyl trans-4-cyanocyclohexanecarboxylate, 4-(2-ethylhexyloxyphenyl) trans-4-cyanocyclohexanecarboxylate, trans-4-n-propylcyclohexyl trans-4-cyanocyclohexanecarboxylate, trans-4-n-heptylcyclohexyl trans-4-cyanocyclohexanecarboxylate, 4-(trans-4-methylcyclohexyl)-phenyl trans-4-cyanocyclohexanecarboxylate, 4-(trans-4-n-butylcyclohexyl)-phenyl trans-4-cyanocyclohexanecarboxylate, 4-(trans-4-n-hexylcyclohexyl)-phenyl trans-4-cyanocyclohexanecarboxylate, 4-n-pentylbiphenyl-4'-yl trans-4-cyanocyclohexanecarboxylate, 4-ethylbiphenyl-4'-yl trans-4-cyanocyclohexanecarboxylate, 4-n-propyloxybiphenyl-4'-yl trans-4-cyanocyclohexanecarboxylate, 4-n-octyloxybiphenyl-4'-yl trans-4-cyanocyclohexanecarboxylate, 4-(4-n-pentylcyclohexyl)-cyclohexyl all-trans-4-cyanocyclohexanecarboxylate, 4-(4-n-hexylcyclohexyl)-cyclohexyl all-trans-4-cyanocyclohexanecarboxylate, 4-(4-n-pentylcyclohexanoyloxy)-cyclohexyl all-trans-4-cyanocyclohexanecarboxylate, m.p. 110°, c.p. 135°; 4-(4-n-heptylcyclohexanoyloxy) cyclohexyl all-trans-4-cyanocyclohexanecarboxylate, m.p. 113°, c.p. 138°; 4-(4-n-nonylcyclohexanoyloxy)-cyclohexyl all-trans-4-cyanocyclohexanecarboxylate, m.p. 116°, c.p. 131°.

EXAMPLE 2

A solution of 2.1 g of 4-n-pentylbenzoyl chloride in 30 ml of diethyl ether is added dropwise to a solution of 1.8 g of trans-4-bromocyclohexanol and 0.8 g of pyridine in 30 ml of diethyl ether at room temperature. The reaction mixture is stirred at room temperature for 12 hours and is filtered off from precipitated pyridine hydrochloride, the filtrate is extracted by shaking successively with 20 ml each of 2 N aqueous hydrochloric acid and 5% aqueous sodium bicarbonate solution, and the organic phase is dried over magnesium sulfate. The resulting ethereal solution of trans-4-bromocyclohexyl 4-n-pentylbenzoate is added to a solution of 1.4 g of boron trifluoride etherate in 50 ml of diethyl ether at 0°, and a solution of 1.2 g of sodium borohydride in 20 ml of diethylene glycol dimethyl ether is added to the resulting mixture at this temperature, while stirring. The reaction mixture is stirred for a further hour at 0° and is then heated to the boil for a further hour. After the reaction mixture has cooled, it is extracted by shaking with 100 ml of water, and the ether phase is separated off and dried over magnesium sulfate. After the solvent has been distilled off, the residual trans-4-bromocyclohexyl 4-n-pentylbenzyl ether is taken up in 35 ml of ethanol, and a solution of 2 g of potassium cyanide in 10 ml of water is added to the solution. The reaction mixture is heated to the boil for 3 hours and then poured into 50 ml of water, and the resulting mixture is extracted by shaking twice, each time with 60 ml of diethyl ether. The ether extracts are dried over magnesium sulfate and evaporated, and the residual trans-4-cyanocyclohexyl 4-n-pentylbenzyl ether is recrystalized from petroleum ether (boiling range 30°-40° C.).

The following compounds are prepared analogously: trans-4-cyanocyclohexyl 4-n-heptylbenzyl ether, trans-4-cyanocyclohexyl 4-ethylbiphenylmethyl ether, trans-4-cyanocyclohexyl 4-(trans-4-n-propylcyclohexyl)-benzyl ether, all-trans-4-cyanocyclohexyl 4-n-butylcyclohexylmethyl ether, all-trans-4-cyanocyclohexyl 4-(4-n-hexylcyclohexyl)-cyclohexylmethyl ether, trans-4-cyanocyclohexylmethyl 4-n-octylphenyl ether, all-trans-4-cyanocyclohexylmethyl 4-n-pentylcyclohexyl ether, all-trans-4-cyanocyclohexylmethyl 4-(4-n-heptylcyclohexyl)-cyclohexyl ether, trans-4-cyanocyclohexylmethyl 4-n-octyloxybiphenyl -4'-yl ether and trans-4-cyanocyclohexylmethyl 4-(trans-4-n-pentylcyclohexyl)-phenyl ether.

EXAMPLE 3

A solution of 6 g of 4-cyanocyclohexanone in 50 ml of diethyl ether is added dropwise, while stirring, at room temperature and during the course of 1.5 hours, to a Grignard solution prepared from 13 g of 1-(4-n-pentylphenyl)-2-bromoethane and 1.3 g of magnesium turnings in 200 ml of diethyl ether. The reaction mixture is then heated under reflux to the boil for 2 hours, and, after it has cooled, 150 ml of 10% aqueous ammonium chloride solution is added to it, while stirring. The ether phase is separated off, dried over sodium sulfate and evaporated. The residual 1-(4-n-pentylphenyl)-2-(4-cyano-1-hydroxycyclohex-1-yl)-ethane is dissolved in 40 ml of acetone and this solution is heated to the boil for 1 hour with 0.5 g of p-toluenesulfonic acid. The solvent is then distilled off and the residue is taken up in 100 ml of ethanol. After the addition of 20 mg of copper (II) sulfate, 23 g of hydrazine hydrate and 40 ml of 30% aqueous hydrogen peroxide solution are added successively to the mixture at 0°. The reaction mixture is stirred for 1 hour at room temperature and poured into 500 ml of water, and the 1-(4-n-pentylphenyl)-2-(trans-4-cyanocyclohexyl)-ethane thus obtained is extracted with diethyl ether; the extracts are dried with sodium sulfate and evaporated, and the residue is recrystallized from isopropanol.

The following compounds are prepared analogously: 1-(4-n-hexyloxyphenyl)-2-(trans-4-cyanocyclohexyl)-ethane, 1-(trans-4-n-butylcyclohexyl)-2-(trans-4-cyanocyclohexyl)-ethane, 1-[(trans-4-n-propylcyclohexyl)-phenyl]-2-(trans-4-cyanocyclohexyl)-ethane, 1-(4-n-pentyloxybiphenyl-4'-yl)-2-(trans-4-cyanocyclohexyl)-ethane, 1-(4-n-heptylbiphenyl-4'-yl)-2-(trans-4-cyanocyclohexyl)-ethane and all-trans-1-[4-(ethylcyclohexyl)-cyclohexyl]-2-(4-cyanocyclohexyl)-ethane.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

We claim:

1. A cyclohexylcarbonitrile derivative of the formula

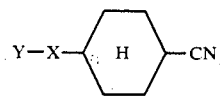

wherein Y is

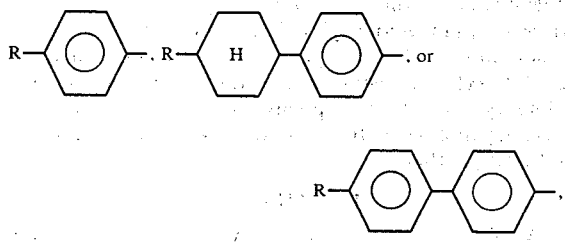

X is —COO—, —O—CO, —CH$_2$O—, —OCH$_2$— or —CH$_2$CH$_2$—, and R is alkyl or alkoxy each of 1–12 carbon atoms; and all cyclohexyl rings are trans.

2. A compound of claim 1 wherein R is straight chained.

3. A compound of claim 1 or 2 wherein when Y is 4-R-phenyl, R is C$_{2-11}$-alkyl or C$_{1-10}$ alkoxy; and when Y is 4-R-biphenyl-4'-yl, or 4-(4-R-cyclohexyl)-phenyl, R is C$_{2-8}$-alkyl or C$_{1-6}$ alkoxy.

4. A liquid-crystalline dielectric comprising at least 2 liquid-crystalline components wherein at least one such component is a cyclohexylcarbonitrile derivative of claim 1.

5. An electro-optical display element having a liquid crystal cell comprising a liquid-crystalline dielectric, wherein the dielectric is one of claim 4.

6. A cyclohexylcarbonitrile derivative of the formula

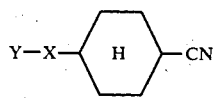

wherein Y is

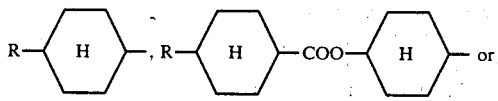

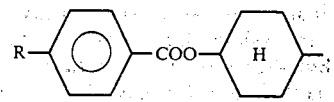

X is —CH$_2$CH$_2$—, and R is alkyl or alkoxy each of 1–12 carbon atoms; and all cyclohexyl rings are trans.

7. A cyclohexylcarbonitrile derivative of the formula

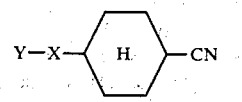

wherein Y is

X is —COO—, —O—CO or —CH$_2$CH$_2$, and R is alkyl or alkoxy each of 1–12 carbon atoms; and all cyclohexyl rings are trans.

8. A compound of claim 6 wherein when Y is 4-R-cyclohexyl, R is C$_{3-10}$-alkyl or C$_{2-8}$ alkoxy; and when Y is 4-(4-R-cyclohexanoyl- or benzoyl-oxy)-cyclohexyl, R is C$_{2-8}$-alkyl or C$_{1-6}$ alkoxy.

9. A compound of claim 7 wherein when Y is 4-(4-R-cyclohexyl)-cyclohexyl, R is C$_{2-8}$-alkyl or C$_{1-6}$ alkoxy.

10. A compound of claim 6 wherein R is straight chained.

11. A compound of claim 7 wherein R is straight chained.

12. A liquid crystalline dielectric comprising at least 2 liquid crystalline components wherein at least one such component is a cyclohexylcarbonitrile derivative of claim 6.

13. A liquid crystalline dielectric comprising at least 2 liquid crystalline components wherein at least one such component is a cyclohexylcarbonitrile derivative of claim 7.

14. An electro-optical display element having a liquid crystal cell comprising a liquid crystalline dielectric, wherein the dielectric is one of claim 12.

15. An electro-optical display element having a liquid crystal cell comprising a liquid crystalline dielectric, wherein the dielectric is one of claim 13.

16. A compound of claim 1 wherein X is —O—CO, —CH$_2$O—, —OCH$_2$— or —CH$_2$CH$_2$—.

17. A compound of claim 1 wherein X is —O—CO, —CH$_2$O— or —OCH$_2$.

18. A compound of claim 7 wherein X is —O—CO or —CH$_2$CH$_2$—.

19. A compound of claim 1 wherein R is alkoxy of 1–12 carbon atoms.

20. A compound of claim 1 wherein Y is

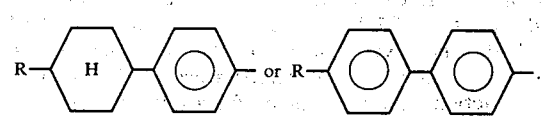

* * * * *